Figure 1:
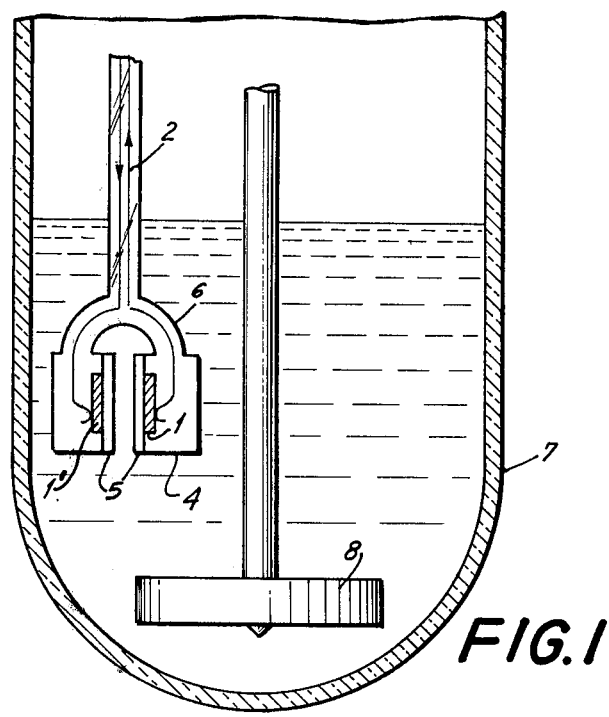

United States Patent [19]

Docekal et al.

[11] 4,327,587
[45] May 4, 1982

[54] METHOD OF AND APPARATUS FOR THE CONTINUOUS MEASUREMENT OF CHANGES IN RHEOLOGICAL PROPERTIES OF MONOMERS DURING POLYMERIZATION

[75] Inventors: Jiri Docekal, Brno; Ludvik Parma, Prague; Ivan Pelant, Prague; Petr Sladky, Prague; Josef Zdravil, Brno, all of Czechoslovakia

[73] Assignee: Vyzkumny ustav chemickych zrizeni, Brno, Czechoslovakia

[21] Appl. No.: 61,621

[22] Filed: Jul. 30, 1979

[30] Foreign Application Priority Data

Aug. 1, 1978 [CS] Czechoslovakia ............... 5055-78

[51] Int. Cl.³ ........................................... G01N 29/02
[52] U.S. Cl. ................................... 73/590; 73/597; 73/599
[58] Field of Search .............. 73/590, 597, 599, 53

[56] References Cited

U.S. PATENT DOCUMENTS

| | | | |
|---|---|---|---|
| 3,087,138 | 4/1963 | Toulis | 73/597 |
| 3,413,595 | 11/1968 | Babikov et al. | 73/597 |
| 3,562,237 | 2/1971 | Thomas | 526/88 |
| 3,654,072 | 4/1972 | Massa | 73/590 |
| 3,737,844 | 6/1973 | Yokoyama et al. | 73/599 |
| 4,145,917 | 3/1979 | Brazhnikov et al. | 73/53 |

Primary Examiner—Anthony V. Ciarlante

[57] ABSTRACT

Method of and apparatus for the continuous measurement of changes in rheological properties of monomers during polymerization. Longitudinal ultrasonic oscillations are introduced into the polymerizing system, and oscillations received after passage through a part of the polymerization system are monitored as the polymerization process proceeds. The ultrasonic oscillations have a frequency of 0.02 to 100 MHz. The monitoring may be of the absorption of the oscillations and/or the rate of propagation of the oscillations.

8 Claims, 2 Drawing Figures

METHOD OF AND APPARATUS FOR THE CONTINUOUS MEASUREMENT OF CHANGES IN RHEOLOGICAL PROPERTIES OF MONOMERS DURING POLYMERIZATION

The invention relates to the method of an apparatus for the continuous measurement of changes in the rheological properties of monomers, such a vinyl chloride, during the polymerization process.

During the production of ployvinylchloride, vinyl chloride polymerizes at tempertures ranging from 40° to 80° C. in a double-wall reactor provided with a mixing propeller and possibly also with a reflux condenser. In the course of the ploymerization process there appear changes in the temperature, pressure, rheological and other physico-chemical quantities. Most of these quantities are usually measured, the temperature and pressure values of the polymerizing system, together with the cooling water temperature being recorded. These quantities, however, provide only incomplete information as to the course of the polymerization process, which is of little advantage with respect to their possible application in the feedback control of the process or for the prediction and signalling of the beginning of emergency situations, such as polymerization fouling of the reflux condenser tubes, etc. In order to obtain more complete information on the process of the polymerization of vinyl chloride or other monomers it is therefore desirable to carry out continuous measurement of changes in the rheological (Rheology is the study of the deformation and flow of matter) properties during the polymerization process.

Current methods and apparatus for the measurement of changes in rheological properties of monomers during polymerization have been based mostly on samples taken at various stages of the polymerization process, and on visual evaluation of such samples, and possibly also on their evaluation by means of other physico-chemical measuring methods.

A disadvantage of these inspection methods and checking apparatus can be seen in the very necessity of taking samples and subsequently evaluating them. The measuring methods used in evaluating the samples taken and in determining the changes in the rheological properties of the polymerizing system are rather complicated and lengthy so that there is a delay in the final determination of the values. This is a great disadvantage, especially when the rheological properties of the polymerizing system and those of the sample taken change differently with time. These circumstances make it difficult to intervene immediately into the polymerization process, not to mention utilizing the values measured for the feedback control of the process.

Another considerable disadvantage of the methods based on taking samples is also the fact that they require human attendance and are dependent on it.

Another considerable disadvantage of the methods based on taking samples is also the fact that they require human attendance and are dependent on it.

Also known are low-frequency ultransonic measuring methods and apparatus which make it possible continuously to measure changes in the viscosity of the polymerizing system during the polymerization process; these work on the principle of scanning the damped oscillations of a metallic waveguide in a viscous medium. A drawback of these measuring methods and apparatus is that viscosity values can be monitored or detected in this way only in the close vicinity of the waveguide, such values in the first approximation being given by the inverse value of the absorption coefficient of the shearing sound waves of the frequency used. Hence it follows that these types of apparatus are sensitive to polymerization fouling of the surface of the monitoring means or of the transmitting sonic probe.

The drawbacks mentioned above are absent in the method and apparatus of the invention for continuous measuring of changes in rheological properties of monomers during the polymerization process.

In the method according to the invention ultrasonic waves of a frequency from 0.02 to 100 MHz are introduced into the polymerizing system, with the absorption and rate of propagation of these waves being monitored and measured during the polymerization process, either on one or more frequencies.

The measured quantities of the absorption and rate of propagation of longitudinal ultrasonic waves correlate with the real and imaginary parts of the complex sheering viscosity. In addition, the magnitude of the absorption and rate of propagation of longitudinal ultrasonic waves in dependence on frequency correlate with the mean value of the diameter and with the shape of the particles of the polymerizing system monomer/polymer.

The main advantages of the method of the invention consist in that it offers the possibility of continuously and smoothly measuring the rheological volume properties during polymerization, such properties being for example, complex viscosity, mean diameter and shape of the particles of the system; it also enables discovering the appearance of local cavitations and of the gaseous phase of the monomer, which lead to the foaming of the system and to polymerization fouling of the reflux condenser. On the basis of spectral dependence of the absorption values or of the rate of propagation of longitudinal ultrasonic waves measured, it is possible to determine optimum parameters of the polymerization process of the individual monomers and to predict the final properties of the polymer.

The apparatus designed to practice the method according to the invention is characterized by containing at least one ultrasonic transducer that is adapted for both generating and receiving longitudinal ultrasonic waves and which is acoustically coupled with an ultrasonic delay line located in the polymerizing monomer.

In the simplest case, the function of both transmitting and receiving ultrasonic waves is performed by a single ultrasonic transducer arranged for reflection. In this case the reflector is the polymerizing medium itself or possibly the wall of the reaction vessel.

In another embodiment, the apparatus employs two ultrasonic transducers, one of which is adapted for generating and the other for receiving longitudinal ultrasonic waves. The two transducers are coupled acoustically with their own delay lines.

In the arrangement with two transducers, i.e. in the throughflow arrangement, two alternatives are possible: The two ultrasonic transducers are either placed in an integrated manner in the polymerizing monomer or one of them is located in the polymerizing medium while the other is disposed outside the reaction vessel but is acoustically coupled with the polymerizing monomer, e.g. by means of the vessel jacket.

With all these alternatives, the ultrasonic transducers are advantageously located in holders which together with delay lines form the pressure and electric insulation jacket of the trasducer.

The ultrasonic transducers may be either of the narrow-band or broad-bank type; their frequency range is chosen such that the absorption values of longitudinal ultrasonic waves in the polymerization, exceed the range of the electronic apparatus used.

An advantage of the apparatus according to the invention is, above all, the application of ultrasonic transducers to the generation and reception of longitudinal ultrasonic waves via ultrasonic delay lines, which enable a continuous introduction and scanning of longitudinal ultrasonic oscillations in the polymerizing system and, simultaneously, enable the measuring of absorption and rate of propagation of longitudinal ultrasonic waves with respect to both the throughflow (passage) when there are two transducers, and the reflection when there is one transducer and a reflector.

With this method the effect of the film of polymer sedimenting at the delay line faces on the magnitude of the quantities measured is substantially limited. The quantities are measured as to their volume, provided the wavelength is at least ten times greater than the thickness of the sedimenting film, and ten times smaller than the distance between the transmitting and the receiving faces of the ultrasonic delay line. The value of the continuously scanned quantity of the absorption coefficient of longitudinal ultrasonic waves can also be used for the feedback control of the polymerization process. Even when only current structural materials are used, the method and the apparatus according to the invention make it possible to design equipment which complies with CSN Standards for electric-spark safety, and the apparatus is pressure-resistant in the range from 0.1 to 500 MPa.

Figure 2:
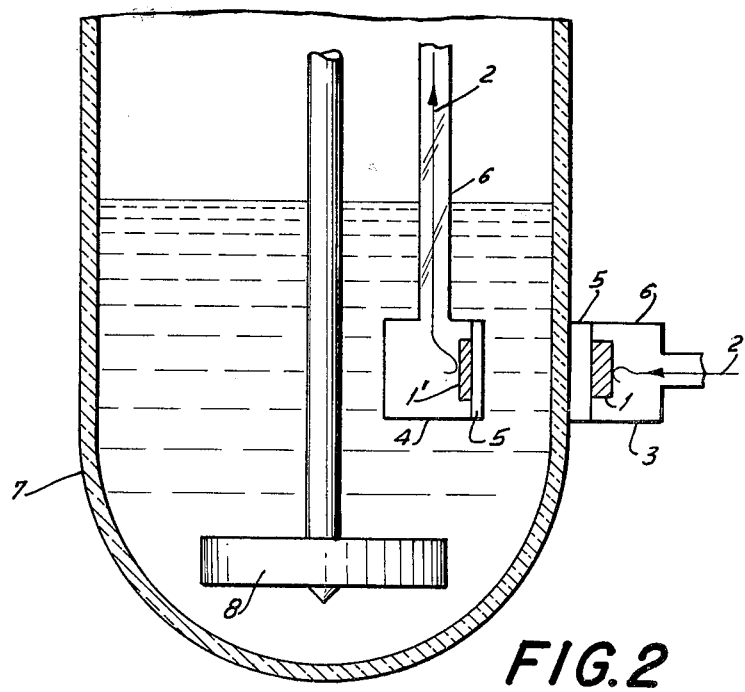

Preferred examples of the apparatus according to the invention are shown in the accompanying drawings in which:

FIG. 1 is a view in vertical axial section of a first embodiment of polymerizing reactor provided with two integrated ultrasonic transducers, and FIG. 2 is a similar view of a second embodiment of polymerizing reactor provided with separate transducers.

Turning first to FIG. 1, the measuring equipment consists of two ultrasonic transducers; transducer 1 is the transmitting transducer, designed for the generation of longitudinal ultrasonic waves, transducer 1' is the receiving transducer, designed to detect these waves. The transducers 1 and 1' are provided with electric leads 2 and are fixed in holders 3 and 4, respectively.

The two transducers 1 and 1' are located in the polymerizing medium, inside a double-walled reactor vessel 7, equipped with a radial propeller 8. The transducers 1 and 1' are acoustically coupled with ultrasonic delay lines 5, which together with holders 3 and 4 form part of the pressure and electric insulation jacket 6.

In FIG. 2, elements which are the same as, or similar to, those of FIG. 1 are designated by the same reference characters.

In the embodiment of FIG. 2, only transducer 1' is located in the reaction vessel 7, while transducer 1 is mounted on the outer wall of the vessel 7. As in FIG. 1, the transducers 1 and 1' are acoustically coupled with ultrasonic delay lines 5, which together with holders 3 and 4 form part of the pressure and electric insulation jacket 6.

The apparatus of FIG. 1 and that of FIG. 2 for continuous measuring of the changes in rheological properties of monomers, such as vinyl chloride, during the polymerization process operates as follows: The measuring apparatus is put into the vessel 7 of the polymerization reactor in such a way that both the ultrasonic probes, i.e. the probes of the transducer 1 and 1' (FIG. 1), or at least one of them (FIG. 2) if completely immersed in the polymerizing system. e.g. vinyl chloride, in the carrier medium.

Fed into the transmitting transducer are radio-frequency pulses of the carrier frequency equal to one of the harmonic frequencies of the ultrasonic transducers 1 and 1', in the simplest case in the form of quasi-monochromatic pulses, e.g. of a frequency of 0.35 MHz and a pulse length of 15 us, with their damping and possibly also the rate of propagation during the passage through the polymerizing vinyl chloride measured in dependence on polymerization time.

The length, repetition rate and amplitude of rf pulses are chosen such that the radiated power of longitudinal ultrasonic waves transmitted into the polymerizing system and its carrier medium does not affect the course of polymerization.

The values measured of absorption or of the rate of propagation of longitudinal ultrasonic waves are compared with the values of model polymerization or they are further processed in electronic circuits to be used for feedback control of the process, for indicating emergency conditions, etc. The measuring and recording of absorption and rate of propagation of ultrasonic signals are carried out by well-known methods of physical acoustics and electronics.

Analogously, the measurement is carried out also for other frequencies of longitudinal ultrasonic waves for the identical polymerization cycle with the result that the spectral dependence of the quantities measured and the optimum value of the frequency measured are obtained.

With the aid of a more sophisticated electronic and ultrasonic equipment it is also possible to introduce into the polymerizing system longitudinal ultrasonic oscillations in the form of videopulses, which having passed through the polymerizing medium are monitored while a rapid spectral and amplitude analysis is simultaneously carried out.

The method according to the invention can, of course, be also applied to measuring changes in rheological volume properties of other monomers during their polymerization; its application is possible with all types of polymerization such as emulsion, solution or precipitation, stereospecific, and also to bulk polymerizations.

Although the invention is illustrated and described with reference to a plurality of preferred embodiments thereof, it is to be expressly understood that it is in no way limited to the disclosure of such a plurality of preferred embodiments but is capable of numerous modifications within the scope of the appended claims.

What is claimed is:

1. The method of continuous measurement of changes in the rheological properties of monomers during a polymerization process, comprising stirring the polymerizing system, and introducing into the stirred polymerizing system longitudinal ultrasonic oscillations of a frequency of from 0.02 to 100 MHz, monitoring the rate of propagation of oscillations received after passage through a part of the polymerization system as the polymerization process proceeds.

2. The method according to claim 1, wherein the ultrasonic oscillations are propagated and received by transducers each having a delay line with a transmitting and a receiving face respectively, the transmitting and receiving faces of the ultrasonic delay lines facing each other, the wave length of the oscillations being greater than the thickness of the sedimenting film of polymer on the delay line faces, the wave length of the oscillations being smaller than the distance between the transmitting and the receiving faces of the delay lines.

3. An apparatus for the continuous measurement of changes in the rheological properties of monomers during a polymerization process, comprising means to contain a polymerization system, means to stir the polymerization system, means to introduce into the stirred system longitudinal ultrasonic oscillations of a frequency from 0.02 to 100 MHz, and means to monitor oscillations received after passage through a part of the stirred polymerization system as the polymerization process proceeds, said last named means comprising two ultrasonic transducers, one of such transducers being adapted for generating longitudinal ultrasonic waves and the other of such transducers being adapted for receiving such waves, the two transducers being acoustically coupled and each having its own ultrasonic delay lines.

4. An apparatus according to claim 3 wherein the two ultrasonic transducers are located in the polymerizing monomer above the means to stir the polymerization system.

5. An apparatus according to claim 3, wherein polymerization takes place within a reaction vessel, and one of the ultrasonic transducers is located in the polymerizing monomer and the other is located outside the reaction vessel, said other transducer being acoustically coupled with the polymerizing monomer.

6. An apparatus according to claim 5, the vessel has a wall, and wherein the other transducer is acoustically coupled with the polymerizing monomer via the wall of the vessel.

7. An apparatus according to claim 6, wherein the ultrasonic transducers are located in holders, which together with delay lines form a pressure and electric insulation jacket for the transducers.

8. An apparatus according to claim 3, wherein the means to introduce into the system longitudinal ultrasonic oscillations and the means to receive oscillations after their passage through a part of the system are constituted by ultrasonic transducer means disposed in a holder which together with delay lines form a pressure and electric insulation jacket for the transducer means.

* * * * *